(12) United States Patent
Ye

(10) Patent No.: US 9,126,929 B2
(45) Date of Patent: Sep. 8, 2015

(54) (S)-4-HYDROXY-2-OXO-1-PYRROLIDINEACETAMIDE RACEMATE CRYSTAL FORM II AND PREPARATION METHOD THEREFOR

(75) Inventor: Lei Ye, Chongqing (CN)

(73) Assignee: Chongqing Runze Pharmaceutical Co., Ltd., Chongqing (CN)

( * ) Notice: Subject to any disclaimer, the term of this patent is extended or adjusted under 35 U.S.C. 154(b) by 0 days.

(21) Appl. No.: 14/237,894

(22) PCT Filed: Apr. 24, 2012

(86) PCT No.: PCT/CN2012/074582
§ 371 (c)(1),
(2), (4) Date: Apr. 10, 2014

(87) PCT Pub. No.: WO2013/020391
PCT Pub. Date: Feb. 14, 2013

(65) Prior Publication Data
US 2014/0235871 A1 Aug. 21, 2014

(30) Foreign Application Priority Data
Aug. 11, 2011 (CN) .............................. 201110230244

(51) Int. Cl.
*C07D 207/273* (2006.01)
(52) U.S. Cl.
CPC .................................. *C07D 207/273* (2013.01)

(58) Field of Classification Search
None
See application file for complete search history.

(56) References Cited

FOREIGN PATENT DOCUMENTS

CN 102101836 A * 6/2011

OTHER PUBLICATIONS

Machine translation of description of CN102101836A (Jun. 22, 2011).*

* cited by examiner

*Primary Examiner* — Michael Barker
(74) *Attorney, Agent, or Firm* — Leong C. Lei

(57) ABSTRACT

An (S)-4-hydroxy-2-oxo-1-pyrrolidine acetamide racemate referred to as (S)-oxiracetam crystal form II has a diffraction peak at a diffraction angle 2θ of 10.669, 13.25, 13.847, 14.198, 16.729, 17.934, 18.746, 18.816, 20.273, 20.413, 21.431, 21.617, 21.663, 23.38, 24.324, 24.415, 26.069, 26.107, 27.901, 28.621, 28.925, 29.449, 29.484, 31.702, 36.516, 37.685, or 39.721 degrees. The purity of the (S)-oxiracetam crystal form II can be up to 98.5%, and the (S)-oxiracetam crystal form II has the advantages of simple preparation method, mild control condition, low production cost, and the produced oxiracetam hydrate crystal form II has a high purity (the oxiracetam hydrate crystal form having a purity of 8%~98.5% can be prepared by a crude levo-oxiracetam having a purity of 92%, and thus having a good reproducibility in production.

6 Claims, 5 Drawing Sheets

(S)-4-HYDROXY-2-OXO-1-PYRROLIDINEACETAMIDE RACEMATE CRYSTAL FORM II AND PREPARATION METHOD THEREFOR

FIELD OF THE INVENTION

The present invention relates to a (S)-4-hydroxy-2-oxo-1-pyrrolidine acetamide racemate crystal form II drug, in particular to a (S)-4-hydroxy-2-oxo-1-pyrrolidine acetamide racemate crystal form II and its preparation method.

BACKGROUND OF THE INVENTION

Oxiracetam (Olaxiracetam) is a nootropic drug which was first synthesized by Smithkline Beecham (Italia) and launched to the market in 1987. (S)-oxiracetam is a single enantiomer with a chemical name of (S)-4-hydroxy-2-oxo-1-pyrrolidine acetamide racemate crystal form II (hereinafter referred to as "(S)-oxiracetam) and a chemical structure as shown below.

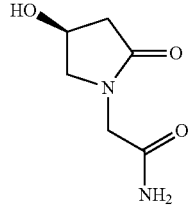

Oxiracetam is capable of promoting the synthesis of phosphorylcholine and phosphoryl ethanol, promoting brain metabolism, and providing a stimulating effect to specific central nervous pathway through blood brain barrier to improve the ATP/ADP ratio of the brain and enhance the synthesis of brain protein and nucleic acid, so as to improve the memory and learning ability of mentally retarded patients, and the drug itself is not vascular active or causes any stimulation to the central nervous system, but this drug has a persistent promoting effect on learning and memory.

P.R.C. Pat. Nos. CN1513836, CN1948285 and CN101121688 have disclosed methods for synthesizing a racemate composed of two isomers, respectively: L-oxiracetam and R-oxiracetam. P.R.C. Pat. Nos. CN101367757 and CN101575309 have disclosed methods for preparing L-oxiracetam. P.R.C. Pat. Nos. CN1424034, CN1555794, CN1562000 and CN101152175 have disclosed methods for preparing oxiracetam injection agent, dispersible tablets, and lyophilized as well as a new formulation. International Pat. No. WO 93/06826 has discloses a method for improving the treatment effect with regard to intelligence by oxiracetam. However, there is no report related to the levo-oxiracetam yet.

SUMMARY OF THE INVENTION

Therefore, it is a primary objective of the present invention to provide a (S)-oxiracetam crystal form II that has the feature of a high purity and provides a good medical treatment effect for improving intelligence.

At present, there is no report related to the (S)-oxiracetam crystal form, and the inventor of the present invention names the (S)-oxiracetam crystal form as (S)-oxiracetam crystal form II.

Another objective of the present invention is to further provide a preparation method of the (S)-oxiracetam crystal form II, and the preparation method is simple and has the features of low cost, and the produced (S)-oxiracetam has a low impurity (or high purity).

To achieve the aforementioned objective, the present invention provides a (S)-oxiracetam crystal form II having a diffraction peak at a diffraction angle 2θ such as 10.669, 13.25, 13.847, 14.198, 16.729, 17.934, 18.746, 18.816, 20.273, 20.413, 21.431, 21.617, 21.663, 23.38, 24.324, 24.415, 26.069, 26.107, 27.901, 28.621, 28.925, 29.449, 29.484, 31.702, 36.516, 37.685, or 39.721 degrees.

The (S)-oxiracetam crystal form II has X-ray diffraction powder data expressed by the following d (Å) values and relative intensity percentage I values (%):

| d value | I value | d value | I value |
|---------|---------|---------|---------|
| 8.2857  | 9       | 6.6765  | 11      |
| 6.3903  | 13      | 6.2329  | 21      |
| 5.2953  | 13      | 4.9422  | 54      |
| 4.7298  | 33      | 4.7123  | 14      |
| 4.3769  | 47      | 4.3471  | 58      |
| 4.1429  | 100     | 4.1077  | 11      |
| 4.099   | 34      | 3.8018  | 9       |
| 3.6563  | 11      | 3.6429  | 44      |
| 3.4154  | 26      | 3.4104  | 40      |
| 3.1951  | 14      | 3.1164  | 16      |
| 3.0843  | 13      | 3.0306  | 19      |
| 3.0271  | 9       | 2.8202  | 26      |

The (S)-oxiracetam crystal form II has a X-ray diffraction powder chart as shown in FIG. 1.

The infrared spectrum of the (S)-oxiracetam crystal form II of the present invention shows an absorption peak occurred at the following wave numbers: 3318 (cm$^{-1}$), 3223 (cm$^{-1}$), 2929 (cm$^{-1}$), 2875 (cm$^{-1}$), 1680 (cm$^{-1}$), 1487 (cm$^{-1}$), 1402 (cm$^{-1}$), 1276 (cm$^{-1}$), 1220 (cm$^{-1}$), 1078 (cm$^-$), 968 (cm$^{-1}$), 943 (cm$^{-1}$), 694 (cm$^{-1}$), or 611 (cm$^{-1}$).

The preparation method of a (S)-oxiracetam crystal form II comprises the following steps:

(1) Dissolve a crude (S)-oxiracetam (purity≤92 wt %) in water, allow the solution to stand still at 5~10° C. for 1~3 days to obtain a colorless transparent crystal, wherein the mass/volume ratio (g/ml) of the (S)-oxiracetam and water is 1:0.7~1.

(2) Filter the colorless transparent crystal, and top wash the colorless transparent crystal with ice water, wherein the mass/volume ratio (g/ml) of the colorless transparent crystal and ice water is 1:1~2, and the temperature of the ice water is 0~5° C.;

(3) Dry the above product in vacuum to obtain a (S)-oxiracetam hydrate crystal form.

The present invention has the following effects:

The (S)-oxiracetam crystal form II of the present invention has a high purity as high as 99%, which has significant treatment effect on improving intelligence, and the preparation method of the (S)-oxiracetam crystal form II is simple and has the features of simple manufacturing method, mild control condition, and low production cost, and the purity of the (S)-oxiracetam hydrate crystal form is very high, wherein the purity (92%) of the crude levo-oxiracetam) can be improved to 99% which is applicable for mass production. In the meantime, the preparation method of the present invention is certain and has good recurrence of obtaining the (S)-oxiracetam hydrate crystal form II of the present invention.

DESCRIPTION OF THE PREFERRED EMBODIMENTS

Figure 1:
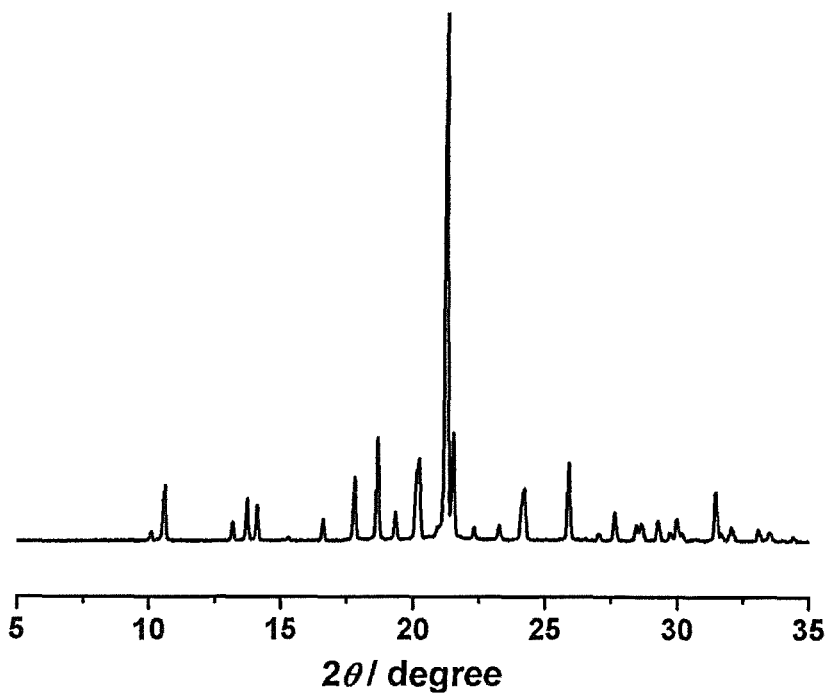
FIG. 1 is a powder diffraction chart of (S)-oxiracetam hydrate crystal form.

The aforementioned and other objectives and advantages of the present invention will become clearer in light of the following detailed description of an illustrative embodiment of this invention. It is intended that the embodiments disclosed herein are to be considered illustrative rather than restrictive.

Preferred Embodiment 1

Dissolve 50 mg of a crude 4-hydroxy-2-oxo-1-pyrrolidineacetamide racemate in an anhydrous methanol, stir the solution overnight, filer the solution, allow the solution to stand still in a dryer, and evaporate the solvent to obtain a colorless transparent crystal with a yield rate of 82% and a purity of 99.4%.

Preferred Embodiment 1

A preparation method of the preparation method of (S)-oxiracetam comprises the following steps:

Dissolve 1 g of crude (S)-oxiracetam (with a purity of 92%) into 0.8 ml of water. Allow the solution to stand still at 7~8° C. for 1~3 days. Filter the solution to obtain a colorless transparent crystal. Top wash the colorless transparent crystal with 1.5 ml of ice water (1~2° C.). Dry the transparent colorless crystal in vacuum at room temperature to obtain 0.7 g of colorless crystal with a purity of 98%.

Preferred Embodiment 2

A preparation method of a (S)-oxiracetam comprises the following steps:

Dissolve 1 g of crude (S)-oxiracetam (with a purity of 90%) in 1 ml of water, allow the solution to stand still at 5° C. for 2~3 days to obtain a colorless transparent crystal, filter the colorless transparent crystal, top wash the colorless transparent crystal with 1 ml of ice water (5° C.), dry the colorless transparent crystal in vacuum at room temperature to obtain 0.6 g of colorless transparent crystal with a purity of 99%.

The crude (S)-oxiracetam is synthesized according to the following steps:

(a) Put 518.4 g of glycinamide hydrochloride, 394 g of sodium bicarbonate and 3.7 L of anhydrous ethanol into three reaction flasks respectively, and control the pH value to approximately 7.4, stir the solution to increase the temperature until a reflux occurs;

(b) Drop 781.6 g of S-4-chloro-3-hydroxybutyrate after the reflux takes place for 2 hours. In the dropping process, 8 patches of the remaining of 394 g of the sodium bicarbonate are added, and the pH value is checked and controlled for each time when the alkaline is added, so as to ensure the pH value≤8.5.

(c) After the dropping, (S)-4-chloro-3-hydroxybutyrate is refluxed for 24 hours until the HPLC testing product (S)-4-hydroxy-2-oxo-1-pyrrolidinyl acetamide content reaches 75%, and the crude (S)-4-hydroxy-2-oxo-1-pyrrolidinyl acetamide is obtained after the heating, filtering and concentrating processes.

(d) The above-mentioned crude product is dissolved in 800 ml of water, and processed by 8.0 L of 001×7 strong acidic styrene cation-exchange resin, and the product is collected. Use 201×7 strong alkaline styrene anion-exchange resin for neutralization and collect the resulted aqueous solution. The neutralization is determined to be finished when the pH value of the solution reaches 7.0±0.1.

Preferred Embodiment 3

The parameters of the crystalline (S)-oxiracetam are measured and tested as follows.

A Bruker D8 Advanced Diffractometer is used to obtain a powder diffraction chart of the crystalline (S)-oxiracetam hydrate of Preferred Embodiment 1 and the testing conditions are listed below: Cu Kα, 40 kV, 40 mV is the light source, the step length is 0.18°, the scanning speed is 4°/min, the scanning range is 5~45°, and room temperature. In the powder X-ray diffraction chart, the crystalline 4-hydroxy-2-oxo-1-pyrrolidineacetamide racemate crystal form has a diffraction peak at a diffraction angle 2θ including 10.669, 13.25, 13.847, 14.198, 16.729, 17.934, 18.746, 18.816, 20.273, 20.413, 21.431, 21.617, 21.663, 23.38, 24.324, 24.415, 26.069, 26.107, 27.901, 28.621, 28.925, 29.449, 29.484, 31.702, 36.516, 37.685 and, 39.721 degrees as shown in FIG. 1.

In the powder X-ray diffraction chart, the crystalline (S)-oxiracetam hydrate of the present invention is expressed by a lattice spacing d, a Bragg angle (2θ) and a relative intensity percentage I as follows:

| 2θ/degree | d/Å | Relative Intensity I/% |
|---|---|---|
| 10.669 | 8.2857 | 9 |
| 13.25 | 6.6765 | 11 |
| 13.847 | 6.3903 | 13 |
| 14.198 | 6.2329 | 21 |
| 16.729 | 5.2953 | 13 |
| 17.934 | 4.9422 | 54 |
| 18.746 | 4.7298 | 33 |
| 18.816 | 4.7123 | 14 |
| 20.273 | 4.3769 | 47 |
| 20.413 | 4.3471 | 58 |
| 21.431 | 4.1429 | 100 |
| 21.617 | 4.1077 | 11 |
| 21.663 | 4.099 | 34 |
| 23.38 | 3.8018 | 9 |
| 24.324 | 3.6563 | 11 |
| 24.415 | 3.6429 | 44 |
| 26.069 | 3.4154 | 26 |
| 26.107 | 3.4104 | 40 |
| 27.901 | 3.1951 | 14 |
| 28.621 | 3.1164 | 16 |
| 28.925 | 3.0843 | 13 |
| 29.449 | 3.0306 | 19 |
| 29.484 | 3.0271 | 9 |
| 31.702 | 2.8202 | 26 |

An Oxford Gemini S Ultra single-crystal diffractometer having a graphite monochromator is used to test the crystalline levo-oxiracetam hydrate crystal structure of the L-crystal structure of Preferred Embodiment of the present invention at 150(2)K. Cu Kα ray (1.54178 Å) is used to collect data by a ω/2θ scanning method. Rigaku RAPID AUTO (Rigaku, 1998, Ver2.30) package program is provided for data restoration and absorption correction. The space group is confirmed by the extinction law of the system, and verified by the refined result. All crystal structures are obtained directly by using the SHELXS-97 program, and the SHELXL-97 program corrects the structure by the full-matrix least square method, and the hydrogen atom coordinates are added by theoretical calculation. The crystallographic Parameter Table of the crystalline (S)-oxiracetam hydrate is shown below:

| Crystallographic Parameter Table of Crystalline (S)-oxiracetam hydrate | |
|---|---|
| Molecular formula | $C_{12}H_{22}N_4O_7$ |
| Molecular weight | 334.34 |
| Testing temperature | 150(2) K |
| Wavelength | 1.54178 Å (Cu Kα) |
| Crystal, space group | Orthogonal, P2(1)2(1)2(1) |
| Lattice parameter | a = 9.4245(3) Å, α = 90o |
| | b = 9.4597(3) Å, β = 90o |
| | c = 17.3882(6) Å, γ = 90o |
| Lattice Volume | 1550.21(9) Å$^3$ |
| Z value, theoretical density | 4, 1.433 g/cm$^3$ |
| Linear absorption coefficient | 1.010 mm$^{-1}$ |
| Structure factor F(000) | 712 |
| Crystal size | 0.10 × 0.14 × 0.10 mm |
| Data collection range θ | 5.09~62.53° |
| Crystal face index | −10 <= h <= 9, −9 <= k <= 9, −14 <= l <= 19 |
| Total number of diffraction points/number of independent diffraction points | 4524/2269 [Rint = 0.0265] |
| Integrity rate (θ = 26.00°) | 98.9% |
| Absorption correction method | Ψ-scanning |
| Max/Min transmittance | 0.9058/0.8799 |
| Refining method | Based on full-matrix least square method of F$^2$ |
| Independent diffraction point data/limitation/refined parameters | 2421/0/208 |
| Goodness of fit factor (GOOF) value | 1.095 |
| R factor [I > 2σ(I)]* | $R_1$ = 0.0298, $wR_2$ = 0.0697 |
| R factor (all data) | $R_1$ = 0.0338, $wR_2$ = 0.0730 |
| Max. residual electron peak/valley | 0.146 /−0.146 e · Å$^3$ |

*$R_1 = \Sigma||F_o| - |F_c||/\Sigma|F_o|$, $wR_2 = [\Sigma w(F_o^2 - F_c^2)^2/\Sigma w(F_o^2)^2]^{1/2}$, $w = [\sigma^2(F_o) + (0.1(\max(0, F_o^2) + 2F_c^2)/3)^2]^{-1}$ FIG. 1 shows a powder x-ray diffraction chart (PXRD) of (S)-oxiracetam hydrate crystal form of the present invention.

Figure 2:
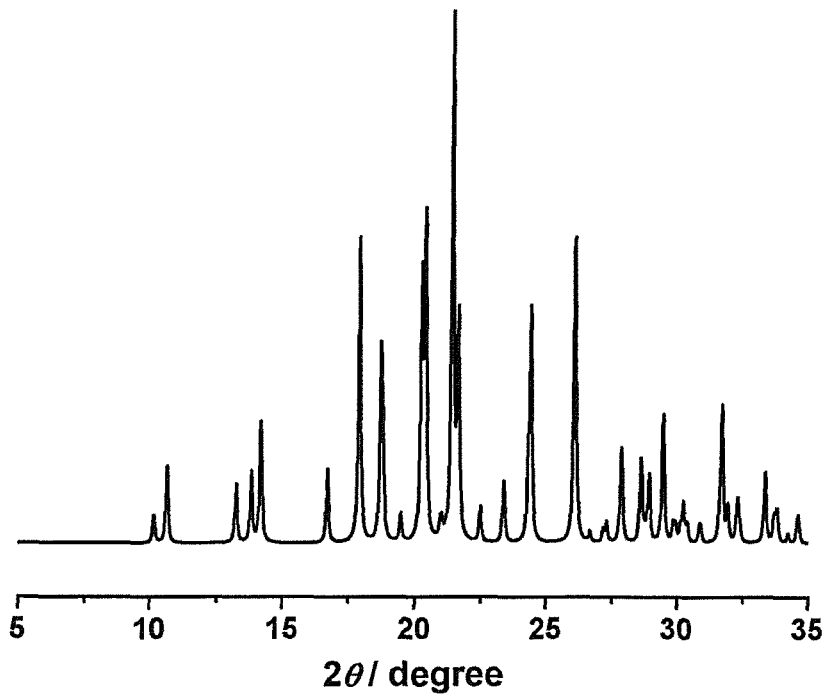
FIG. 2 is powder diffraction chart showing the number of single crystal structures of a crystalline (S)-oxiracetam according to a simulation.

FIG. 2 is a powder x-ray diffraction chart showing the number of single crystal structures of a crystalline (S)-oxiracetam according to a simulation, and the peaks of FIGS. 1 and 2 are overlapped, and it shows that the prepared crystalline (S)-oxiracetam hydrate is simply of a single crystal form.

Figure 3:
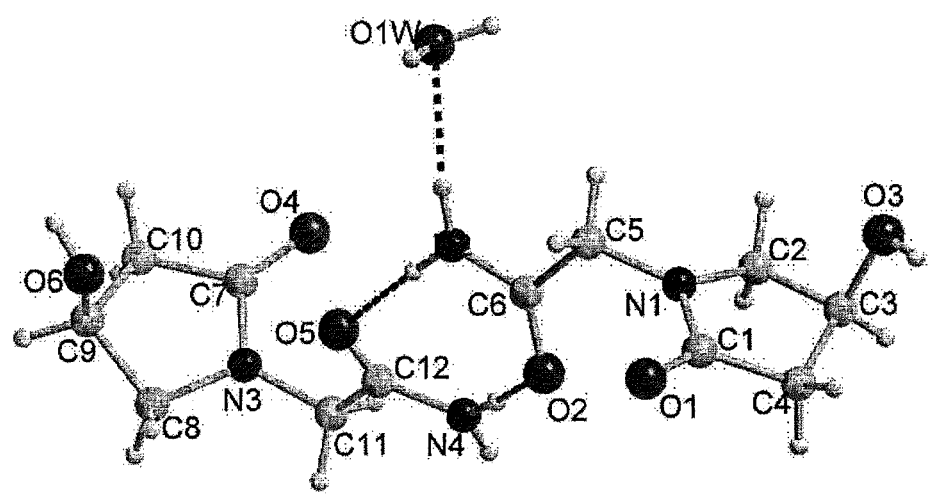
FIG. 3 is a structural view of a single-crystal (S)-oxiracetam hydrate crystal form II.

FIG. 3 shows a single-crystal structure of the (S)-oxiracetam.

Figure 4:
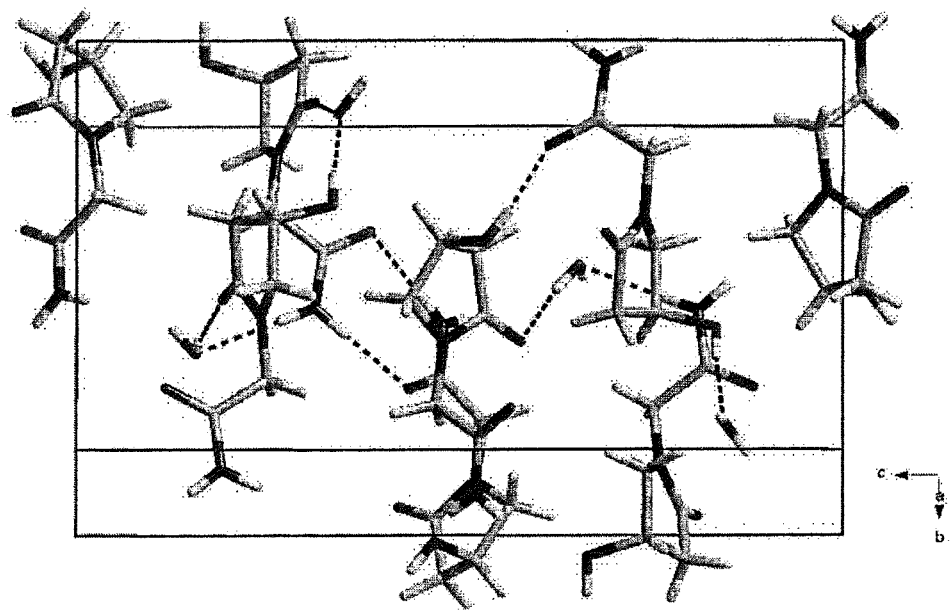
FIG. 4 is a crystal packing diagram of a (S)-oxiracetam hydrate crystal form II.

FIG. 4 is a crystal packing diagram of a (S)-oxiracetam hydrate.

Figure 5:
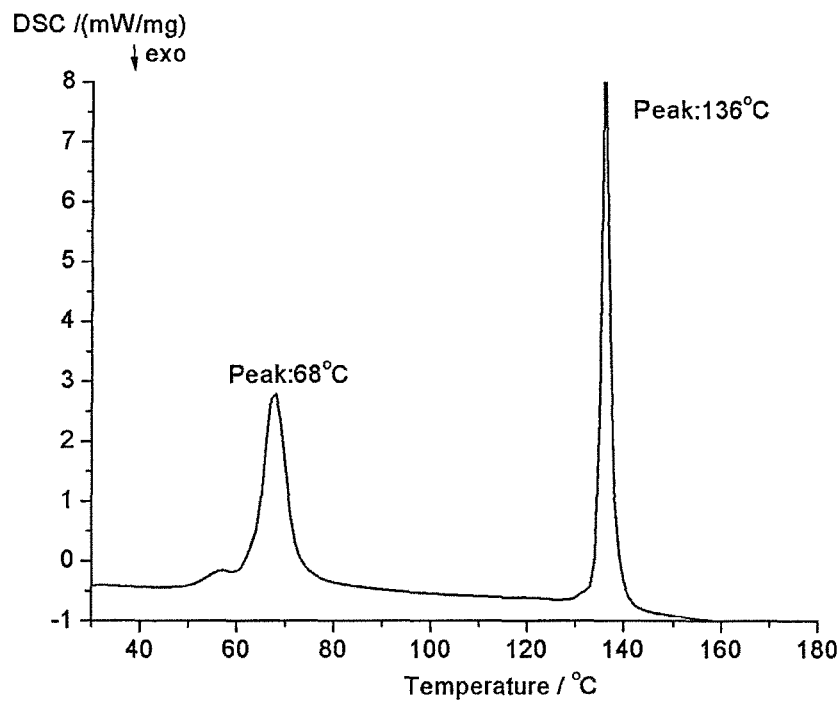
FIG. 5 is a differential scanning calorimetry chart (DSC) of a (S)-oxiracetam hydrate crystal form II.
Figure 6:
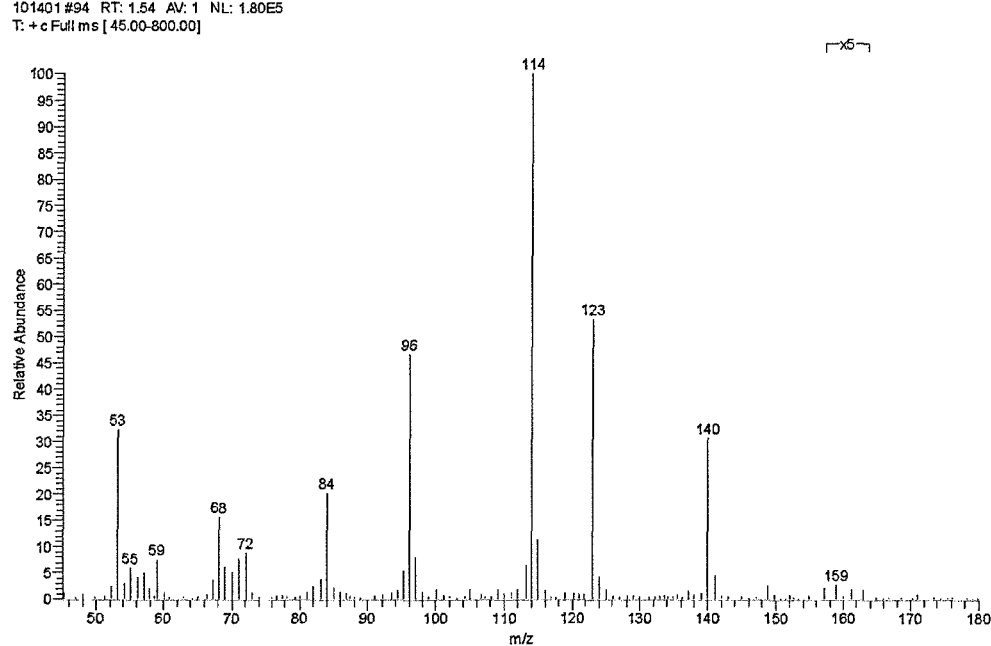
FIG. 6 is an electron ionization mass-spectrometry (EI-MS) chart of a (S)-oxiracetam hydrate crystal form II.

FIG. 5 is a differential scanning calorimetry chart (DSC) of a (S)-oxiracetam hydrate, and the heat absorption transition temperature is at 68° C. and 136° C.;

FIG. 6 is an electron ionization mass-spectrometry (EI-MS) chart of a (S)-oxiracetam hydrate.

Figure 7:
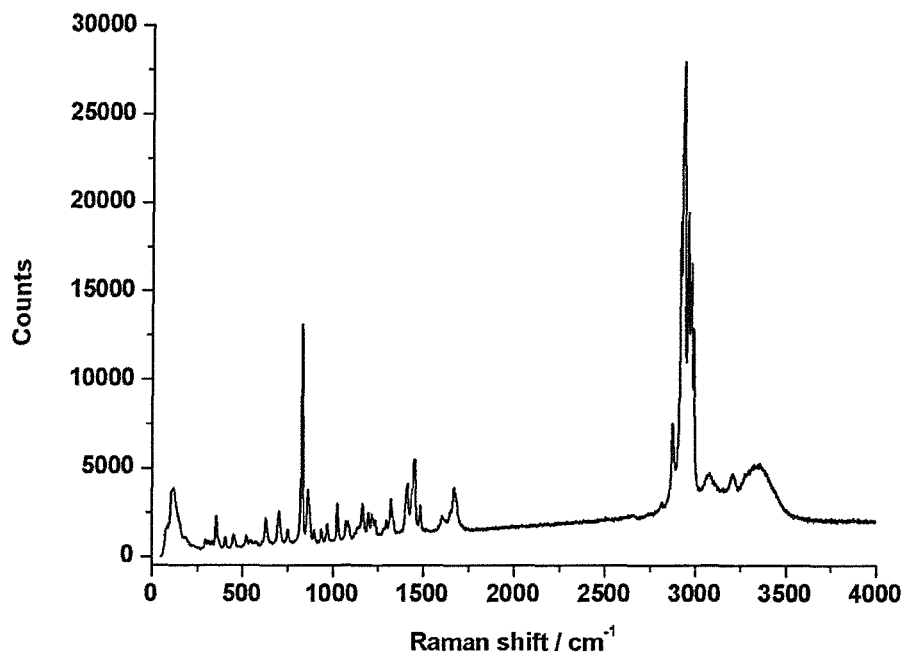
FIG. 7 is a Raman spectroscopy of a (S)-oxiracetam hydrate crystal form II.

FIG. 7 is a Raman spectroscopy of a (S)-oxiracetam hydrate crystal.

Figure 8:
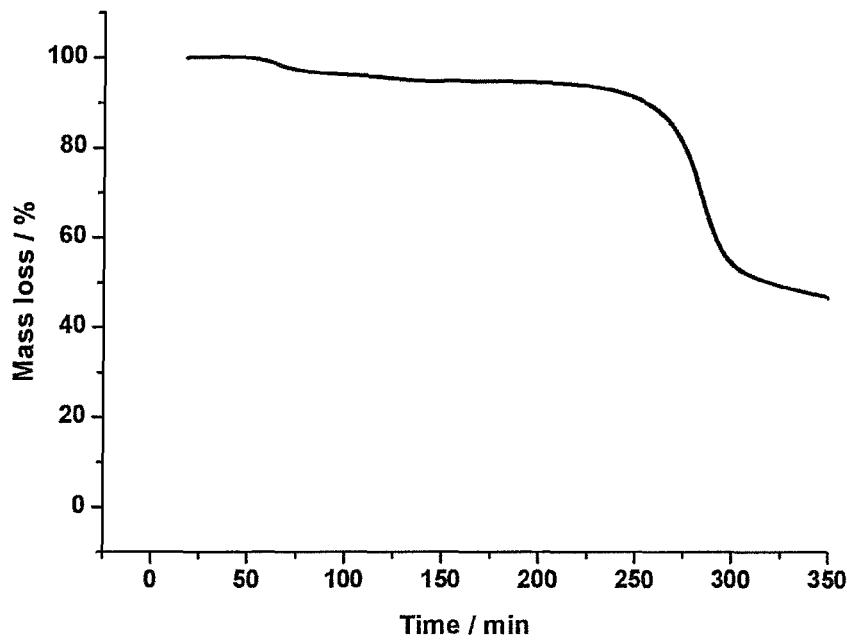
FIG. 8 is a thermal gravimetric analysis (TGA) chart of a (S)-oxiracetam hydrate crystal form II.

FIG. 8 is a thermal gravimetric analysis (TGA) chart of a (S)-oxiracetam hydrate.

Figure 9:
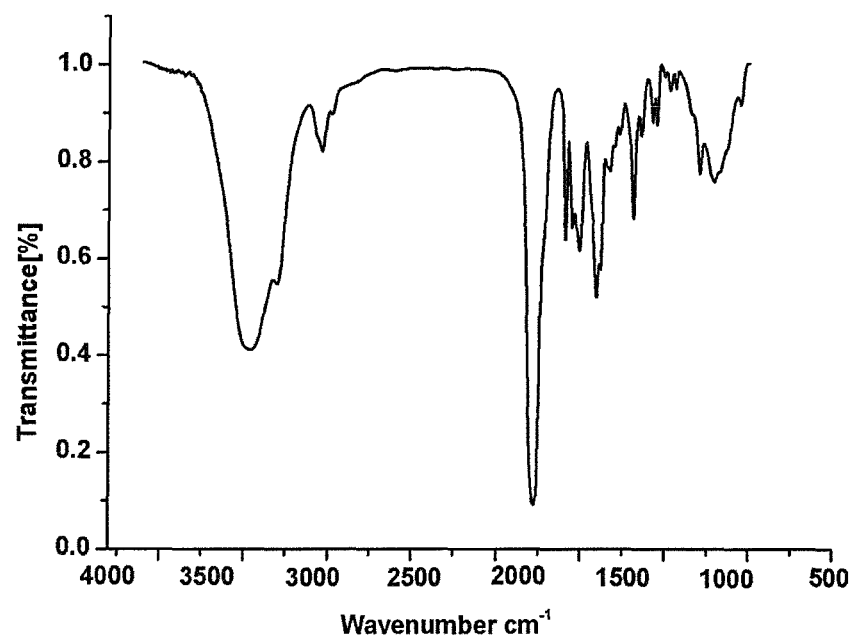
FIG. 9 is an infrared spectrometry (IR) chart of a (S)-oxiracetam hydrate crystal form II.

FIG. 9 is an infrared spectrometry (IR) chart of a (S)-oxiracetam hydrate crystal, and there is a peak at a wave number of 3318, 3223, 2929, 2875, 1680, 1487, 1402, 1276, 1220, 1078, 968, 943, 694, or 611.

Tests show that the powder x-ray diffraction chart of the Preferred Embodiment 2 is the same as the powder x-ray diffraction chart of the Preferred Embodiment 1. Obviously, the method of the present invention has excellent recurrence to obtain a crystalline (S)-oxiracetam hydrate stably.

While the invention has been described by means of specific embodiments, numerous modifications and variations could be made thereto by those skilled in the art without departing from the scope and spirit of the invention set forth in the claims.

What is claimed is:

1. A (S)-4-hydroxy-2-oxo-1-pyrrolidineacetamide racemate crystal form II, having a diffraction peak at a diffraction angle 2θ selected from the group consisting of 10.669, 13.25, 13.847, 14.198, 16.729, 17.934, 18.746, 18.816, 20.273, 20.413, 21.431, 21.617, 21.663, 23.38, 24.324, 24.415, 26.069, 26.107, 27.901, 28.621, 28.925, 29.449, 29.484, 31.702, 36.516, 37.685, and 39.721 degrees.

2. The (S)-4-hydroxy-2-oxo-1-pyrrolidineacetamide racemate crystal form II according to claim 1, having X-ray diffraction powder data expressed by the following d (Å) values and relative intensity percentage I values (%),

| d value | I value | d value | I value |
|---|---|---|---|
| 8.2857 | 9 | 6.6765 | 11 |
| 6.3903 | 13 | 6.2329 | 21 |
| 5.2953 | 13 | 4.9422 | 54 |
| 4.7298 | 33 | 4.7123 | 14 |
| 4.3769 | 47 | 4.3471 | 58 |
| 4.1429 | 100 | 4.1077 | 11 |
| 4.099 | 34 | 3.8018 | 9 |
| 3.6563 | 11 | 3.6429 | 44 |
| 3.4154 | 26 | 3.4104 | 40 |
| 3.1951 | 14 | 3.1164 | 16 |
| 3.0843 | 13 | 3.0306 | 1 |
| 3.0271 | 9 | 2.8202 | 26. |

3. The (S)-4-hydroxy-2-oxo-1-pyrrolidineacetamide racemate crystal form II, having an X-ray diffraction powder chart as shown in FIG. 1.

4. The (S)-4-hydroxy-2-oxo-1-pyrrolidineacetamide racemate crystal form II according to any one of claims 1 to 3, having an absorption peak in an infrared spectrum produced by the (S)-4-hydroxy-2-oxo-1-pyrrolidineacetamide racemate crystal form II in a wave number selected from the group consisting of 3318 (cm$^{-1}$), 3223 (cm$^{-1}$), 2929 (cm$^{-1}$), 2875 (cm$^{-1}$), 1680 (cm$^{-1}$), 1487 (cm$^{-1}$), 1402 (cm$^{-1}$), 1276 (cm$^{-1}$), 1220 (cm$^{-1}$), 1078 (cm$^{-1}$), 968 (cm$^{-1}$), 943 (cm$^{-1}$), 694 (cm$^{-1}$), and 611 (cm$^{-1}$).

5. A preparation method of the (S)-4-hydroxy-2-oxo-1-pyrrolidineacetamide racemate crystal form II of any one of the claims 1-3, comprising the steps of:
(1) dissolving a crude (S)-oxiracetam (with a purity≤92 wt %) in water, allow the solution to stand at approximately 5-10° C. for 1-3 days to obtain a colorless transparent crystal, wherein the mass/volume ratio (g/ml) of the (S)-oxiracetam to water is approximately equal to 1:0.7-1;
(2) filtering the colorless transparent crystal, and top-washing the colorless transparent crystal with ice water, wherein the mass/volume ratio (g/ml) of the colorless transparent crystal to ice water is 1:1-2, and the temperature of the ice water is 0-1° C.; and
(3) drying the colorless transparent crystal to obtain the (S)-oxiracetam hydrate crystal form II.

6. A preparation method of the (S)-4-hydroxy-2-oxo-1-pyrrolidineacetamide racemate crystal form II of any one of the claim 4, comprising the steps of:
   (1) dissolving a crude (S)-oxiracetam (with a purity≤92 wt %) in water, allow the solution to stand at approximately 5-10° C. for 1-3 days to obtain a colorless transparent crystal, wherein the mass/volume ratio (g/ml) of the (S)-oxiracetam to water is approximately equal to 1:0.7-1;
   (2) filtering the colorless transparent crystal, and top-washing the colorless transparent crystal with ice water, wherein the mass/volume ratio (g/ml) of the colorless transparent crystal to ice water is 1:1-2, and the temperature of the ice water is 0-1° C.; and
   (3) drying the colorless transparent crystal to obtain the (S)-oxiracetam hydrate crystal form II.

* * * * *